Figure 1:
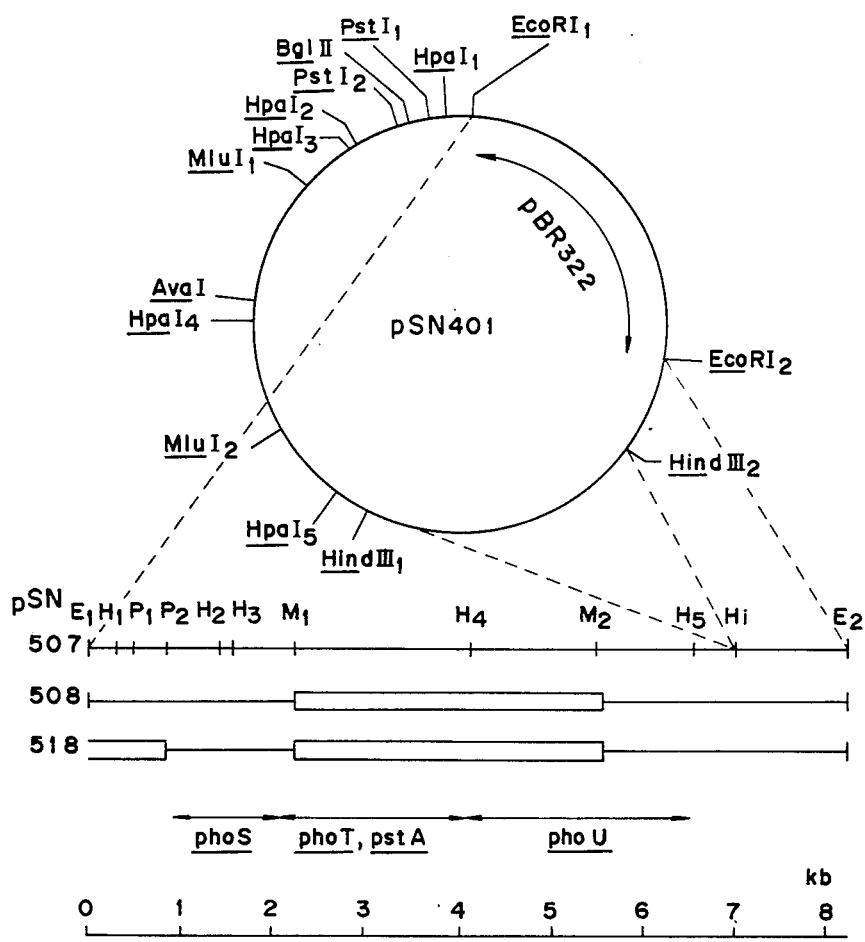

United States Patent [19]

Nakata et al.

[11] Patent Number: 4,703,005
[45] Date of Patent: Oct. 27, 1987

[54] EXPRESSION VECTOR CARRYING A GENE CODING FOR A PHOSPHATE-BINDING PROTEIN, A METHOD FOR PREPARING THE SAME AND A METHOD FOR PREPARING THE SAME AND A METHOD FOR PRODUCING A POLYPEPTIDE USING THE SAME

[75] Inventors: Atsuo Nakata, Toyonaka; Hideo Shinagawa, Minoo, both of Japan

[73] Assignee: The Research Foundation for Microbial Diseases of Osaka University, Osaka, Japan

[21] Appl. No.: 501,559

[22] Filed: Jun. 6, 1983

[30] Foreign Application Priority Data

Jun. 4, 1982 [JP] Japan ................................. 57-96775

[51] Int. Cl.$^4$ ...................... C12P 21/00; C12P 19/34; C12N 15/00; C12N 1/00
[52] U.S. Cl. ......................................... 435/68; 435/91; 435/172.3; 435/253; 435/320; 935/29; 935/41; 935/60; 935/73
[58] Field of Search .............. 435/317, 68, 253, 172.2, 435/172.3, 91; 935/29, 41, 60, 73

[56] References Cited

U.S. PATENT DOCUMENTS

| | | | |
|---|---|---|---|
| 4,237,224 | 12/1980 | Cohen et al. | 435/68 |
| 4,273,875 | 6/1981 | Manis | 435/253 |
| 4,374,927 | 2/1983 | Sninsky et al. | 435/68 |
| 4,375,514 | 3/1983 | Siewert et al. | 435/172 |

FOREIGN PATENT DOCUMENTS

| | | |
|---|---|---|
| 0032238 | 7/1981 | European Pat. Off. |
| 2441659 | 6/1980 | France |
| 2023612 | 1/1980 | United Kingdom |
| 2052516 | 1/1981 | United Kingdom |

OTHER PUBLICATIONS

Amemura et al, 1981, (Abstract), "Cloning of Alkaline Phosphatase Regulatory Genes of *E. coli*", 4th Ann. Meeting of Japan Mol. Biol.
Maniatis et al, 1982, *Molecular Cloning A Laboratory Manual*, Cold Spring Harbor Lab., p. 422.
Iwakura et al, 1982, "Isolation of DNA Fragment Containing the Phos Gene of *Escherichia coli*, K-12", *J. Biochem*, v92, 615-622.
Amemura et al, 1982, "Cloning of and Complementation Tests with Alkaline Phosphatase Regulatory Genes (phoS and phoT) of *E. coli*", J. Bact., v152, 692-701.
Levitz, et al., "Complementation Tests Between Alkaline Phosphatase-Constitutive Mutants (phoS and phoT) of *E. coli*", J. Bact., 1981, vol. 145, pp. 1432-1435.
Zuckier et al., "Genetic and Physiological Tests of Three Phosphate-Specific Transport Mutants of *E. coli*", J. Bact., 1981, vol. 145, pp. 1249-1256.

*Primary Examiner*—Thomas G. Wiseman
*Assistant Examiner*—Karen Maurey
*Attorney, Agent, or Firm*—Armstrong, Nikaido, Marmelstein & Kubovcik

[57] ABSTRACT

An expression vector carrying a gene coding for a phosphate-binding protein has been found to have a strong gene expression. The expression vector can be produced by transforming a bacterium belonging to Enterobacteriaceae with a recombinant vector carrying a DNA fragment containing a gene coding for a phosphate-binding protein to form transformants, selecting the transformants containing the desired recombinant vector from said transformants, and isolating the desired recombinant vector from the selected transformants. The expression vector is useful for producing polypeptides.

7 Claims, 2 Drawing Figures

EXPRESSION VECTOR CARRYING A GENE CODING FOR A PHOSPHATE-BINDING PROTEIN, A METHOD FOR PREPARING THE SAME AND A METHOD FOR PREPARING THE SAME AND A METHOD FOR PRODUCING A POLYPEPTIDE USING THE SAME

The present invention relates to an expression vector, the production of the same and the use of the same. More particularly, the present invention relates to an expression vector having a strong gene expression which carries a gene coding for a phosphate-binding protein, a method for producing the same and a method for producing a desired polypeptide by means of gene expression using said expression vector.

The term "gene expression" as used herein is intended to mean the translation to polypeptide from a gene coding for the sequence of polypeptide. In the gene expression, a DNA chain coding for the sequence of polypeptide is first transcribed to a complementary RNA which is called a messenger RNA and, then, the thus transcribed messenger RNA is translated into the above-mentioned polypeptide.

In 1970, the transformation technique of *Escherichia coli* was established [M. Mandel and A. Higa, Journal of Molecular Biology, 53, 159-162 (1970)], and a restriction enzyme was found [H. O. Smith and K. W. Wilcox, Journal of Molecular Biology, 51, 379-391 (1970)]. These findings brought rapid progress in gene engineering and cell technology. For example, the fundamental technique of genetic recombination disclosed in U.S. Pat. No. 4,237,224 has been established based on such findings. Further, novel vectors have been produced and methods for producing useful substances by gene engineering have been proposed. The above-mentioned novel vectors are disclosed in, for example, German patent application Laid-Open Specification No. 2712615, French patent Specification No. 2441659, U.S. Pat. No. 4,273,875, PCT patent application Publication No. WO 79/01169, British patent Specification No. 2052516 and EPC patent Specification No. 32238. The above-mentioned methods for producing useful substances are disclosed in, for example, U.S. Pat. No. 4,375,514.

However, all of the above publications only disclose that desired useful substances may be produced by means of gene expression. The techniques of the above-mentioned prior art publications have such a drawback that the yield of desired useful substances is not sufficiently high. Therefore, the development of an expression vector capable of producing useful substances in high yield is earnestly desired in the art.

Accordingly, from the standpoint of industrial application of gene engineering and reduction of cost for the production of useful substances, it has been desired in the art to develop an expression vector excellent in power of gene expression. The fundamental techniques of genetic recombination are disclosed in Proceedings of the National Academy of Science, U.S.A., 70, 3240-3244 (1973) and ibid., 71, 1743-1747 (1974), but there has not been proposed a general method for isolating a gene excellent in power of gene expression from a large number of genes present in nature, leading to difficulty in solving the above-mentioned problem.

The present inventors have made extensive and intensive studies to settle the above-mentioned problem. As a result, it has been found that a gene coding for a phosphate-binding protein can provide an expression vector having an extremely strong gene expression as compared with those of the conventionally known vectors. The present inventors then succeeded in preparing such an expression vector carrying a gene coding for a phosphate-binding protein by the technique of cloning, with high efficiency. The present invention has been made, based on such a novel finding and success.

Therefore, it is an object of the present invention to provide an expression vector which is excellent in power of gene expression.

It is another object of the present invention to provide a method for preparing an expression vector which is excellent in power of gene expression.

It is a further object of the present invention to provide a method for producing polypeptides in high yield by means of gene expression using an expression vector of the kind as mentioned above.

Figure 2:
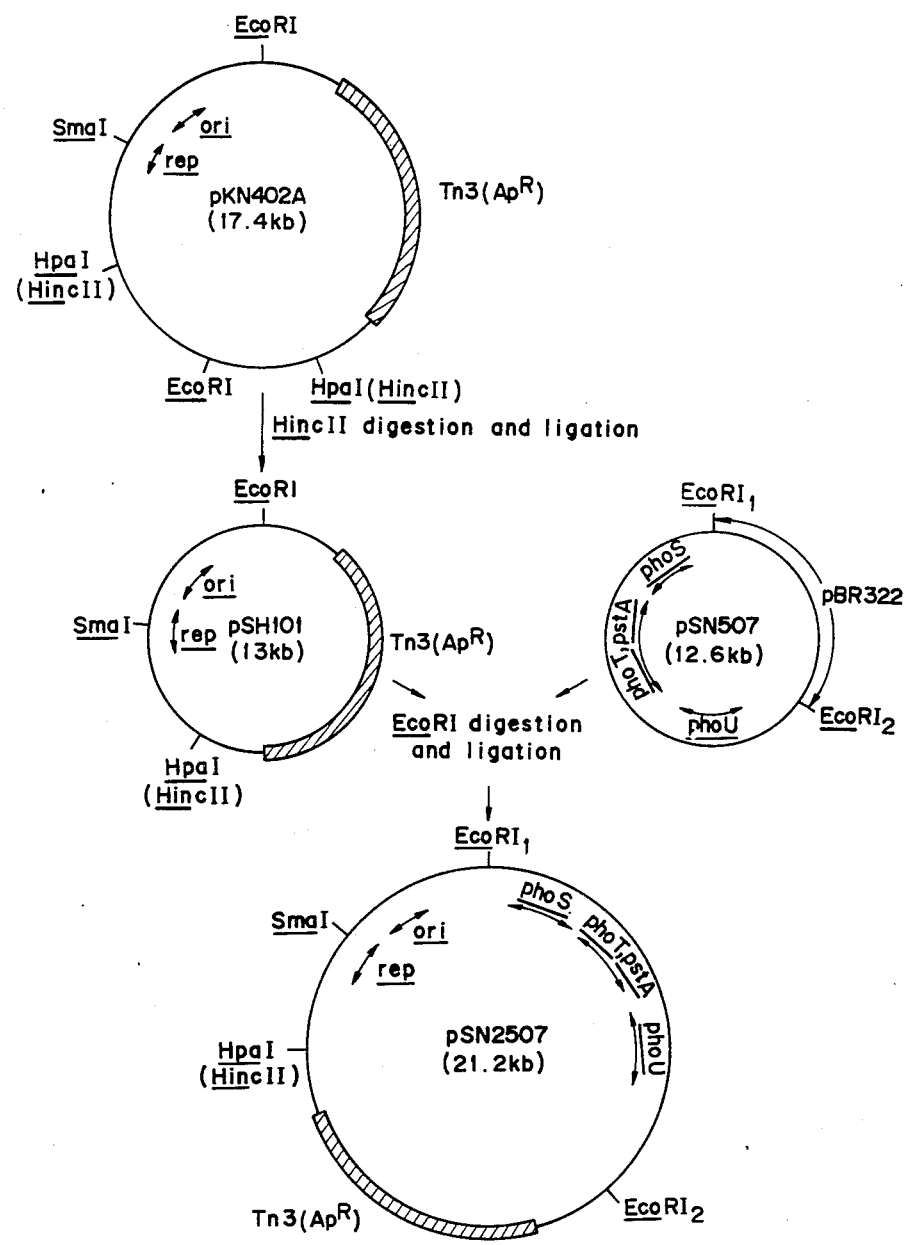

The foregoing and other objects, features and advantages of the present invention will be apparent from the following detailed description taken in connection with the accompanying drawings in which:

FIG. 1 illustrates the restriction maps of plasmids pSN401, pSN507, pSN508 and pSN518; and FIG. 2 illustrates the flow-sheet of the method for the preparation of the plasmid pSN2507, shown with the restriction maps of the plasmids pKN402A, pSH101 and pSN2507.

In FIGS. 1 and 2, the symbol phoS designates a gene coding for a phosphate-binding protein of *Enterobacteriaceae* (on which a detailed explanation will be given later). The symbols *phoT*, *pstA* and *phoU* each designate genes which are clustered on chromosomal DNA of *E. coli* together with *phoS* (on which a detailed explantion will be given later). The following symbols are used to denote recognition sequences for restriction enzymes:

EcoRI, HpaI, PstI, BglII, MluI   .
HindIII, AvaI, HincII and SmaI (the suffix numbers attached to the above-mentioned symbol as shown in FIGS. 1 and 2 are used to identify the respective recognition sites for a restriction enzyme).

Other abbreviations are respectively:

Tn3(Ap$^R$) (indicated by ▨▨▨▨): transponson carrying ampicillin resistance coding gene
Rep: replication gene
ori: replication origin
Kb: 1,000 nucleotide pairs
▭▭▭: deleted portion In one aspect of the present invention, there is provided an expression vector which comprises a DNA fragment including a gene coding for a phosphate-binding protein and a replicon selected from plasmids and bacteriophages, said DNA fragment being ligated to said replicon. The term "replicon" used herein is intended to mean a vector which is replicable and has a gene for a phenotypical trait and a restriction site adopted to ligate a donor DNA fragment thereto.

A replicon is a carrier of genetic information which is known as a replication unit of a chain of nucleotides such that, once replication begins, replication is successively carried out to the end of nucleotide sequence. As such a replicon, there can be mentioned plasmids, bacteriophages, viruses and the like. The replicons include DNA replicons and RNA replicons, but in the present invention the RNA replicons are not preferred from a practical point of view. As the DNA replicons, there can be mentioned plasmids and replicable DNA fragments derived from DNA viruses, procaryotic cells and eucaryotic cells. Among them, as a replicon to be used in the present invention, plasmids and bacteriophages are preferred. Conventionally, DNA replicons carrying a gene conferring antibiotic resistance are widely used for cloning various genes. The widely employed method of cloning a gene comprises digesting chromosomal DNA with a restriction enzyme to obtain a DNA fragment carrying the desired gene, ligating said DNA fragment to said DNA replicon, transforming a unicellular organism with said DNA replicon including said DNA fragment to form transformants, isolating the transformants from parent unicellular organism by means of the antibiotic resistance imparted by said DNA replicon, and incubating the isolated transformants, whereby said DNA replicon including said DNA fragment is cloned.

The gene coding for a phosphate-binding protein is responsible for phosphate transport system and phosphate metabolism system and, evolutionally, exist widely in procaryotic cells and unicellular eucaryotic cells. Aong them, the gene coding for a phosphate-binding protein of *Escherichia coli* has been comparatively well studied in detail, and especially, the gene of *Escherichia coli* is called phoS gene. The phoS gene exists not only in *Escherichia coli* but also in bacteria belonging to Enterobacteriaceae. Accordingly, the phoS gene of any of bacteria belonging to Enterobacteriaceae may be used in the present invention. The phoS of *Escherichia coli* is clustered together with phoT, pstA and phoU at 83 minutes on *E. coli* standard genetic map [Backman, B. J. and K. B. Low, Microbiol. Rev. 44, 1–56 (1980)]. The phoT, pstA and phoU are genes whose function is related to phosphate transport and phosphate metabolism. As mentioned above, the phoS, phoT, pstA and phoU genes are clustered on a chromosome of *E. coli* and, therefore, when a DNA fragment carrying the phoS gene is prepared from chromosomal DNA of *E. coli* by means of a restriction enzyme, the phoT, pstA and phoU genes are also included in the DNA fragment. The gene coding for a phosphate-binding protein of λglmS phage has also been studied, and may be used in the present invention.

Further, genes, whose function is related to phosphate transport system and phosphate metabolism system, of yeast and a bacterium other than a bacterium belonging to Enterobacteriaceae may be used. In this case, it is necessary to choose a replicon and a host suitable for genes, whose function is related to phosphate transport system and phosphate metabolism system, of yeast and a bacterium other than a bacterium belonging to Enterobactericeae.

In another aspect of the present invention, there is provided a method for preparing an expression vector which comprises:

(1) preparing a chromosomal DNA containing a gene coding for a phosphate-binding protein from bacteria belonging to Enterobacteriaceae;

(2) cleaving the chromosomal DNA with a restriction enzyme to provide DNA fragments;

(3) ligating said DNA fragments to a replicon selected from plasmids and bacteriophages;

(4) transforming cells of a bacterium belonging to Enterobacteriaceae with said replicon having the DNA fragment ligated thereto to form transformants including those which contain a recombinant vector including the DNA fragments carrying a gene coding for a phosphate-binding protein;

(5) selecting transformants containing the recombinant vector including the DNA fragments carrying a gene coding for a phosphate-binding protein from said transformants; and (6) isolating the recombinant vector including the DNA fragments carrying the gene coding for a phosphate-binding protein from the selected transformants.

In the step (1) of the method of the present invention, chromosomal DNA containing a gene coding for a phosphate-binding protein (hereinafter referred to simply as "phoS gene") is prepared from bacteria belonging to Enterobacteriaceae by a customary isolation technique such as lysis, centrifugation or the like.

In the step (2), the chromosomal DNA as prepared in the above step (1) is cleaved with a restriction enzyme to provide DNA fragments containing a DNA fragment carrying the phoS gene.

In the step (3) of the method of the present invention, as mentioned above, any of plasmids and bacteriophages may be used as the replicon. The ligation of the DNA fragments to the replicon may be performed by using a ligase according to the customary method (see, for example, U.S. Pat. No. 4,237,224). At least one of the DNA fragment carrying a phoS gene and replicon has a gene for a phenotypical trait.

In the above step (4), cells of a bacterium belonging to Enterobacteriaceae are transformed with the replicon carrying the DNA fragment as prepared in the above step (3). As the bacterium belonging to Enterobacteriaceae, there can be mentioned Escherichia, Enterobacter, Erwinia, Klebsiella, Proteus, Salmonella, Serratia and Shigella. Further, besides the above-mentioned bacteria, there may be used mutant cells of any of the above-mentioned bacteria. It, of course, is necessary to choose the suitable bacterium, taking into consideration replicability of the replicon in the cells of a bacteria. For example, *Escherichia coli,* Serratia species or Salmonella species can be suitably used as the host, when well-known relaxed type plasmid such as pBR322, pBR325, pACYA177 or pKN410 is used as the replicon.

In the above step (5), the transformants are first isolated from parent cells of a bacterium belonging to Enterobacteriaceae by means of the phenotypical trait such as drug resistance imparted by the replicon having gene for a phenotypical trait. Then, transformants containing the recombinant vector including the DNA fragment carrying the phoS gene are selected from the above-isolated transformants using as a criterion the amount of phosphate-binding protein in the transformants. The amount of phosphate-binding protein in each of the transformants is determined as follows. First, the phosphate-binding protein is isolated from the transformant and purified by a customary technique such as lysis, centrifugation, or salting-out. Then, the amount of the purified phosphate-binding protein is determind by a customary technique such as SDS-agarose gel electrophoresis. The amount of the phosphate-binding protein in each of the transformants is compared with the amount of the phosphate-binding protein produced from a parent cell of a bacterium belonging to Enterobacteriaceae not transformed with the replicon carrying the DNA fragment. The transformants having larger amount of phosphate-binding protein than the parent cell of bacterium belonging to Enterobacteriaceae are selected.

In case a mutant cell which produces alkaline phosphatase not only under a phosphate starvation condition but also under a phosphate-rich condition is used as the cell of a bacterium belonging to Enterobacteriaceae in the above step (4), the selection of transformants containing the replicon including the DNA fragment carrying the phoS gene in the above step (5) can be very easily carried out without determination of the amount of the phosphate-binding protein in each of the transformants. The reason for this is as follows. When such a mutant cell is transformed with the replicon carrying the DNA fragment as prepared in the above step (3), the mutant cell produces alkaline phosphatase under a phosphate starvation condition but do not produce alkaline phosphatase under a phosphate-rich condition by means of function of the phoS gene contained in the DNA fragment ligated to the replicon. Therefore, when the transformation is carried out under a phosphate-rich condition, alkaline phosphatase negative transformants are selected.

In the above step (6), the recombinant vector including the DNA fragment carrying the phoS gene is isolated from the transformants selected in the step (5) by a customary technique such as lysis, centrifugation or the like.

On the other hand, it should be noted that an expression vector which carries a gene, whose function is related to phophate transport system and phosphate metabolism system, of yeast or a bacterium other than a bacterium belonging to Enterobacteria may be prepared according to substantially the same method as described above. Further, it is noted that instead of the DNA fragment prepared according to the step (1) and (2) of the above-mentioned method, a DNA fragment prepared from phages such as λglmS phage may be used.

The recombinant vector prepared according to the method as mentioned above may be partially deleted, with respect to the DNA fragment portion and/or the replicon portion, using a restriction enzyme while retaining the phoS gene and subjecting the resulting deleted recombinant vector to religation by means of a ligase, thereby to prepare a reconstructed recombinant vector having a reduced size. The reconstructed recombinant vector becomes easier to manipulate because the number of restriction sites of the reconstructed recombinant vector is decreased as compared with that of the original recombinant vector. Further, when a gene coding for a certain polypeptide is ligated to the reconstructed recombinant vector, the ratio of the length of the gene coding for the polypeptide to the total length of the recombinant vector becomes higher than that in the case where the gene coding for the polypeptide is ligated to the original recombinant vector which is not reconstructed. It is conceivable that the higher the ratio of the length of the gene coding for a polypeptide to the total length of the recombinant vector is, the larger the amount of the protein produced per cell becomes and the less the amount of byproducts produced per cell becomes. Therefore, when the above-mentioned reconstructed recombinant vector is used for producing a certain desired polypeptide, not only the high productivity of the polypeptide can be attained but also the purification of the polypeptide obtained can be achieved with ease.

A DNA fragment carrying phoS gene may be cut out from the recombinant vector as prepared according to the method of the present invention and ligated to a different kind of replicon from the kind of replicon of the original recombinant vector to prepare another type of reconstructed recombinant vector. Such another type of reconstructed recombinant vector can advantageously be used when easy selection of the transformants is intended by changing a phenotypical trait of the replicon and/or an increase is intended in copy number of a recombinant vector. The use of such another type of reconstructed recombinant vector is desirable when the transformants obtained by means of the original recombinant vector are those from which the desired transformants are difficult to select and/or the replicability of the original recombinant vector in the transformants is low.

The reconstruction of the recombinant vector as mentioned above is carried out by a customary technique (see, for example, U.S. Pat. Nos. 4,340,674, 4,349,629 and 4,356,270).

The expression vector prepared according to the method of the present invention can be identified by constructing the restriction map as follows. The expression vector is partially or completely digested with various restriction enzymes to obtain DNA fragments. The obtained fragments are subjected to agarose-gel electrophoresis, thereby to determin the size and restriction pattern of the expression vector. The position of the phoS gene on the above mentioned expression vector is determined by constructing a variety of deletion expression vectors of the present invention by means of partial or complete digestion with an appropriate restriction enzyme and subsequent self-ligation, and examining said deletion expression vectors by the complementation tests using the phoS gene-negative mutant as the host.

The expression vector carrying the phoS gene of the present invention has the following advantages when the gene coding for a desired polypeptide is ligated to said expression vector at its portion downstream of the DNA sequence of a promoter of the phoS gene and the production of the desired polypeptide is conducted by gene techniques:

(1) The yield of the above-mentioned desired polypeptide is as high as $1 \times 10^5 - 10^6$ molecules/cell which is several to 100 times that obtained using the conventionally employed vector.

(2) The gene expression of the expression vector of the present invention can be freely controlled by adjusting the concentration of phosphate in culture medium. Therefore, the production of the desired polypeptide can also be controlled by adjusting the concentration of phosphate in the culture medium.

(3) The desired polypeptide may be secreted together with phosphate-binding protein portion into periplasm of the host. Therefore, the above-mentioned desired polypeptide can be easily isolated from the host.

Therefore, the expression vector of the present invention can be widely used in the industrial application field. An example of the method of producing a desired polypeptide using the expression vector of the present invention will now be explained. The gene coding for the desired polypeptide is prepared from the genes of eucaryotic cells, procaryotic cells or viruses, and the thus prepared gene is ligated to the expression vector of the present invention. Then, the host is transformed with the above-obtained expression vector to form transformants. Subsequently, the thus obtained transformants are incubated on a large scale, thereby to produce the desired polypeptide in extremely high yield.

Thus, in a further aspect of the present invention, there is provided a method for producing a polypeptide by means of gene expression using the expression vector of the present invention which comprises:

(1) ligating a DNA fragment carrying a gene coding for a polypeptide to said expression vector at its portion downstream of the DNA sequence of a promoter of the gene coding for a phosphate-binding protein;

(2) transforming cells of a bacterium belonging to Enterobacteriaceae with said expression vector having the gene coding for a polypeptide ligated thereto to form transformants;

(3) selecting said transformants from parent cells of a bacterium belonging to Enterobacteriaceae;

(4) incubating said transformants, causing said transformants to express the gene coding for the polypeptide and produce the polypeptide; and (5) isolating the polypeptide from the incubated transformants.

In practicing the above-mentioned method, a DNA fragment carrying a gene coding for a polypeptide is first prepared by organic synthesis, or isolated from organisms by a customary technique such as lysis, centrifugation, digestion with a restriction enzyme or the like. It is also possible to prepare a DNA fragment carrying a gene coding for a desired polypeptide from a RNA fragment prepared from messenger RNA and RNA viruses by converting a RNA fragment carrying a desired gene to complementary DNA fragment using well-known reverse transcriptase. The DNA fragment carrying a gene coding for a polypeptide is ligated to an expression vector carrying the phoS gene of the present invention at its portion downstream of the DNA sequence of a promoter of the phoS gene. At least one of the DNA fragment carrying a gene coding for a polypeptide, DNA fragment carrying the phoS gene of the expression vector and replicon of the expression vector has a gene for a phenotypical trait such as drug resistance, enzymatic activity or the like. The portion at which the DNA fragment carrying a gene coding for a polypeptide is ligated to the expression vector may be disposed between the proximal part and the distal part of the DNA fragment carrying the phoS gene, so that a fusion protein can be produced. Said portion may also be disposed downstream of the DNA fragment carrying the phoS gene, so that a hybrid protein can be produced. The above-mentioned ligation process is carried out using a ligase by a customary technique (see, for example, U.S. Pat. No. 4,237,224).

In the above step (2), cells of a bacterium belonging to Enterobacteriaceae are transformed with the expression vector having the gene coding for a polypeptide ligated thereto by a customary method (see, for example, U.S. Pat. No. 4,237,224). As a bacterium belonging to Enterobacteriaceae, there can be mentioned Erwinia, Enterobacter, Escherichia, Klebsiella, Proteus, Salmonella, Serratia and Shigella.

In the above step (3), the transformat is selected from parent cells of the bacterium belonging to Enterobacteriaceae by means of a phenotypical trait, such as drug resistance imparted by the expression vector.

In the above step (4), the transformants are incubated under an appropriate nutrient conditions to the transformants, causing the transformants to express the gene and produce the desired polypeptide therein.

In the above step (5), the isolation of the desired polypeptide from the transformants and purification of the polypeptide are performed by a customary technique such as lysis, salting-out, column chromatography or the like.

In case the gene coding for a desired polypeptide is ligated to the expression vector at its portion downstream of the DNA sequence coding for the signal peptide of a phoS gene in the above step (1), the desired polypeptide produced in the transformants in the above step (4) is secreted the periplas of the transformants. The reason for this is as follows. The above-mentioned signal peptide is coded in the phoS gene on the side of the N-terminal amino acid sequence of a phosphate-binding protein and expressed together with a phosphate-binding protein. The signal peptide is required for interaction with and secretion through the inner membrane of a cell. In other words, the signal peptide plays a role in secreting a phosphate binding protein into the periplasm of a cell through the inner membrane. Therefore, when the transformant containing the expression vector to which the gene coding for a desired polypeptide is ligated at its portion downstream of the DNA sequence coding for the signal peptide of the phoS gene is incubated, the desired polypeptide produced in the transformant is secreted into the periplasm of the transformant by the function of the signal peptide. The polypeptide secreted into the periplasm can be isolated without lysing the transformant and, therefore, the isolation of the produced polypeptide secreted into the periplasm is very easy as compared with that of the polypeptide not secreted into the periplasm.

The expression vector having a gene coding for a polypeptide ligated thereto obtained in the above Step(1) may be reconstructed in substantially the same manner as described before with respect to the reconstruction of the expression vector of the present invention. For example, the expression vector having a gene coding for a polypeptide ligated thereto at a portion such as will give a hybrid protein may be changed to an expression vector having a gene coding for a polypeptide ligated thereto at a portion such as will give a fusion protein.

It is noted that the phoS gene may be ligated to viral genes coding for a desired polypeptide, so that the desired polypeptide coded by the viral gene can be produced efficiently.

As described, the expression vector may be utilized for producing physiologically active substances, enzymes, antigens, toxins, amino acids, secondary metabolites and the like. As the physiologically active peptides, there may be mentioned hormones such as somatostatin, insulin, ACTH, growth hormone and the like, calmodulin, cell growth factors, interferones and the like. As the enzymes, there may be mentioned urokinase, mutanase, amylase, glucoseisomerase, hyaluronidase, reverse transcriptase, enzymes concerning nitrogen fixation and the like. As the antigens, there may be mentioned influenza virus HA antigen, hepatitis B surface antigen and the like. As the toxins, there may be mentioned *Bordetella pertussis* toxin, snake venom and the like. As the amino acids, there may be mentioned L-glutamic acid, L-lysine, L-methionine and the like. As the secondary metabolites, there may be mentioned antibiotics, mycotoxins and the like. As the proteins other than the above-mentioned substances, there may be mentioned opioid peptides, ovalbumin and the like. Therefore, the present invention is very useful to produce foods, drugs, feeds, fermented products, energy sources and the like.

The present invention will be illustrated in more detail with reference to the following Examples, which should not be construed to be limiting the scope of the present invention.

The culture mediums, buffer solutions, methods of extracting DNA and methods of purifying DNA each used in Examples will be summarized below.

A: Composition of T Medium
Bacto-tryptone: 10 g
NaCl: 5 g
The above ingredients were dissolved in 1000 ml of water.

B: Rapid Alkali Extraction of plasmid DNA 0.1 ml of a lysozyme solution [2 mg/ml lysozyme, 50 mM glucose, 100 mM CDTA (cyclohexanediamine tetraacetate), 25 mM trisHCl (pH 8.0)] was added to the bacterial cell pellet obtained from 1.5 ml culture by centrifugation which culture had been incubated overnight. The resulting suspension was incubated at 0° C. for 30 min. Then, 200 µl of an alkaline SDS solution [0.2 N NaOH, 1 w/w% SDS (sodium dodecylsulfate)] was added to the suspension, and agitated. After the incubation at 0° C. for 5 min, 150 µl of 3 M sodium acetate (pH 4.8) was added to the suspension, and gently mixed. The resulting suspension was kept at 0° C. for 60 min, and then subjected to centrifugation at 5000 rpm for 5 min to remove precipitates. From the upper portion of the supernatant, 0.4 ml of an aliquot was pipetted out. The aliquot was mixed with 1 ml of cold absolute ethanol to precipitate the DNA. The resulting mixture was centrifuged for 2 min and, then, the resulting supernatant was discarded and into the resulting pellet was added 100 µl of a sodium acetate solution [0.1 M sodium acetate, 0.05 M tris-HCl (pH 8.0)]. The resulting solution was mixed with 2-time volume of cold absolute ethanol to effect re-precipitation of the DNA. The precipitated DNA was dissolved in an appropriate buffer. The particulars of the above procedures are described in Nucleic Acid Research, Vol. 7 No. 6, pp 1513-1523 (1979). The crude plasmid DNA prepared according to the above-mentioned procedure can be used for physical map analyses and for transformation.

C: Removal of Ethidium Bromide from DNA

The DNA fraction after the CsCl density-gradient centrifugation was mixed with the equal volume of an isopropanol solution saturated with aqueous 5 M NaCl 10 mM tris-HCl-1 mM Na₃EDTA (pH 8.3). The above procedure was repeated until the aqueous phase containing DNA was decolorized. Two volumes of water and then 6 volumes of absolute ethanol were added to the resulting aqueous phase. The mixture was allowed to stand at −20° C. for one hour to several days to precipitate DNA. The precipitated DNA was collected by centrifugation and dried to obtain a DNA sample. The DNA sample was dissolved in 100 µl of a Tris-EDTA solution [10 mM Tris-HCl, 1 mM Na₃EDTA (pH 7.5)] and put to use. The particulars of the above procedures are described in Advanced Bacterial Genetics, p 126, Cold Spring Harbor Laboratory (1980).

D: Composition of EcoRI Restriction Enzyme Buffer (5) fold concentrated)
NaCl: 500 mM
Tris-HCl: 250 mM (pH 7.4)
MgSO4: 50 mM E: Composition of Ligase Buffer
Tris-HCl: 66 mM (pH 7.6)
MgCl₂: 6.6 mM
Dithiothreitol: 10 mM
ATP: 0.5 mM F: CsCl Block Density-Gradient Centrifugation One ml of a 5.0 M CsCl solution [5.0 M CsCl, 10 mM MgSO4, 10 mM Tris-HCl (pH 8.0), 0.1 mM Na₂EDTA (buoyant density=1.60)] was placed in the bottom cellulose nitrate centrifuge tube having a diameter of ⅝ inch and a length of 2 inches (manufactured and sold by Beckman Instruments Inc., U.S.A.). On the solution in the tube, 3 ml of 3.0 M CsCl solution [3.0 M CsCl, 10 mM MgSO4, 10 mM Tris-HCl (pH 8.0), 0.1 mM Na₂EDTA (buoyant density=1.40)] was overlaid. Then, 1 ml of a phage suspension was further overlaid on the CsCl solution layer, and centrifuged at 30,000 rpm in SW 50.1 rotor [manufactured and sold by Beckman Instruments Inc., U.S.A.] at 20° C. for one hour. Then, less than 0.5 ml of phage fraction was removed from side of tube with a 1-ml syringe and a ⅝-inch, 25-gauge needle. The particulars of the above procedures are described in Advanced Bacterial Genetics, pp 80-81, Cold Spring Harbor Laboratory (1980).

G: CsCl Equilibrium Density-Gradient Centrifugation

The phage fraction obtained in Item F above was mixed with a 4.0 M CsCl solution [4.0 M CsCl, 10 mM MgSO4, 10 mM tris-HCl (pH 8.0), 0.1 mM EDTA], and centrifuged at 30,000 rpm in SW 50.1 rotor for 20 hours. No more than 0.5 ml phage fraction was removed from side of tube with a 1-ml syringe and a ⅝-inch, 25-gauge needle. The particulars of the above procedures are described in Advanced Bacterial Genetics, p 81, Cold Spring Harbor Laboratory (1980).

H: Composition of LB Medium *
Bacto-peptone: 10 g
Yeast Extract: 5 g
NaCl: 5 g
The above ingredients were dissolved in 1000 ml of water, and the pH was adjusted to 7.2 by addition of NaOH.

I: Composition of T Agar Medium *
Bacto-triptone: 10 g
NaCl: 5 g
Agar: 15 g

*[Note] After the medium was autoclaved for sterilization, 1/1000 volume of a 10 mg/ml aqueous tetracycline solution or a 40 mg/ml aqueous ampicillin solution was added thereto. The media containing antibiotics were used for selecting antibiotic resistant transformants and ensuring the maintenance of antibiotic resistant recombinant vector in the bacterial cells.

The above ingredients were dissolved in water, and water was further added to such an extent that the whole volume of the solution became 1000 ml.

EXAMPLE 1

Step 1: Preparation of plasmid pBR322 DNA and cleavage of the plasmid pBR322 DNA by restriction enzyme EcoRI 1 Liter of T medium was inoculated with 10 ml of a seed of *Escherichia coli* K-12 strain C600 [B.J. Bachmann, Bacterial. Rev., 36, 525-557 (1972)] (carrying plasmid pBR322), and cultured at 37° C. with shaking until the turbidity of the culture broth reached 0.6 A at 600 nm. Chloramphenicol was added to the culture broth to a final concentration of 250 µg/ml. The culture broth was then incubated at 37° C. for 15 hours, and subjected to centrifugation to collect cells. The thus collected cells were once washed with 100 ml of Tris-EDTA solution [containing 100 mM TrisHCl buffer (pH 7.5) and 1 mM EDTA], and subjected to rapid alkali extraction to obtain a crude plasmid DNA. Into the thus obtained crude plasmid DNA, the above-mentioned Tris-EDTA solution was added in such an amount that the total volume became 15 ml. 16 g of crystal CsCl and 2 ml of 5 mg/ml ethidium bromide were added to the solution, and the specific gravity $d^{25}$ of the mixture was adjusted to 1.39 by adding water or crystal CsCl thereinto. The resulting mixture was then subjected to centrifugation at 33,000 rpm at 20° C. for 40 hours. The position of the band of plasmid DNA was determined by means of ultraviolet light with a long wavelength, and the plasmid DNA was collected by fractionation. From the plasmid DNA fraction, the ethidium bromide was removed by the method as described in item C. To 0.2 ml of the thus obtained pBR322 DNA solution (100 μg/ml), 0.05 ml of restriction enzyme buffer for EcoRI was added, and, to the resultant, restriction enzyme EcoRI was added in such an amount that the activity of restriction enzyme EcoRI became one unit per μg of the plasmid DNA. The enzyme reaction was carried out at 37° C. for 60 minutes. Thereafter, the mixture was heated at 65° C. for 5 minutes to inactivate the restriction enzyme. The mixture was then dialyzed against Tris-EDTA solution [containing 10 mM Tris-HCl (pH 8.0) and 1 mM EDTA]. After completion of the dialysis, 4 units of alkaline phosphatase of *Escherichia coli* (manufactured and sold by Sigma Chemical Co., U. S. A.) was added to the mixture, followed by incubation at 65° C. for 30 minutes. An equal amount of a phenol solution (prepared by saturation of the above-mentioned Tris-EDTA solution with phenol) was added to the mixture, followed by shaking. The resultant was then subjected to low-speed centrifugation, and separated into the aqueous phase and the phenol phase. The aqueous phase was collected. The above-mentioned centrifugation and collection steps were repeated twice. Thereafter, equal volume of solution I (24:1 by volume mixture of chloroform and isoamyl alcohol) was added to the collected aqueous phase. The resultant was well mixed, and the aqueous phase was collected. Such operation was repeated 4 times, and the collected aqueous phase was dialyzed against ligase buffer for the subsequent ligation reaction, whereby a cleaved DNA solution for pBR322 was obtained.

Steps 2: Preparation of DNA fragments containing a DNA fragment carrying the phoS gene from *Escherichia coli* K-12 strain 1 Liter of T medium was inoculated with 10 ml of a seed of *Escherichia coli* K-12 strain KLF48/KL159 (CGSC #4302) [*E. coli* Genetic Stock Center (CGSC), Yale University, Connecticut, U.S.A.], and cultured at 37° C. with shaking. The culture broth in logarithmic growth phase (turbidity: 0.6 A at 600 nm) was subjected to centrifugation to collect cells. The thus collected cells were suspended in 10 ml of lysozyme solution (containing 2 mg/ml lysozyme, 100 mM EDTA and 0.15 M NaCl) and the suspension was allowed to stand at 37° C. for 15 minutes. The suspension was then rapidly frozen on a dry ice/acetone bath at −20° C. Into the thus frozen suspension, 50 ml of a Tris-SDS buffer [containing 0.1 M Tris-HCl (pH 9.0), 1 W/V % SDS (sodium dodecyl sulfate) and 0.1 M NaCl] was added and the result was subjected to melting at 60° C. The above mentioned steps of freezing on a dry ice/acetone bath and melting at 60° C. were repeated five times, whereby the cells were lysed completely. Into the resulting solution in which the cells were lysed, an equal amount of a phenol solution (prepared by saturation of the above-mentioned Tris-SDS buffer with redistilled phenol) was added, followed by stirring. The resultant was then subjected to low-speed centrifugation, whereby it was separated into the aqueous phase and the phenol phase. The aqueous phase was collected. The thus collected aqueous phase was mixed with twice the volume of absolute ethanol. The resulting mixture was then subjected to centrifugation at 12,000 rpm for 20 minutes, and pellets were collected. The thus collected pellets were dissolved in 20 ml of a mixture of NaCl and citric acid (containing 0.15 M NaCl and 0.015 M sodium citrate, pH 7.0), thereby to obtain a solution containing DNA. Into 10ml of the obtained DNA containing solution, an equal amount of the solution I (as mentioned in Step 1) was added, followed by stirring. From the resultant, the aqueous pase was collected. Further, the thus collected aqueous phase was mixed with twice the volume of ethanol, and the precipitated DNA was dissolved in 5 ml of Tris-EDTA solution [containing 10 mM Tris-HCl (pH 7.5) and 1 mM Na₂EDTA]. The precipitation with absolute ethanol as mentioned above was repeated, and 5 ml of DNA solution was prepared. To 0.2 ml of the thus obtained DNA solution (200 μg/ml), 0.05 ml of restriction enzyme buffer was added, and, to the resultant, restriction enzyme EcoRI was added in such an amount that the activity of restriction enzyme EcoRI became one unit per μg of DNA. Then, the mixture was incubated at 37° C. for 60 minutes, followed by heat treatment at 65° C. for 5 minutes to inactivate the restriction enzyme. The mixture was then dialyzed against the ligase buffer, thereby to obtain a *E. coli* DNA solution.

Step 3: Ligation of pBR322 DNA and *E. coli* DNA fragments containing a phoS gene The pBR322 DNA solution as prepared in Step 1 was diluted to 30 μg/ml in DNA concentration with a ligation buffer. The *E. coli* DNA solution as prepared in Step 2 was diluted to 100 μg/ml in DNA concentration with the same ligation buffer as mentioned just above. 50 μl of the pBR322 DNA solution and 100 μl of the *E. coli* DNA solution was mixed. T4 ligase was added to the resulting mixture in an amount of one unit of T4 ligase per μg of DNA to be ligated. The enzyme reaction for ligating the DNAs was conducted at 8° C. for 8 hours. After completion of the ligation, the resulting solution was dialyzed against Tris-EDTA solution [containing 10 mM Tris-HCl (pH 7.5) and 1 mM EDTA].

Step 4: Selection of plasmids carrying the phoS gene

A : *E. coli* C75 strain

*E. coli* C75 strain [Garen, A., and N. Otsuji, J. Mol. Biol., 8, 841–852 (1964 was cultured in LB medium while shaking until the turbidity of the culture broth became 0.6 A at 600 nm. Then, 2.5 ml of the culture broth was subjected to low-speed centrifugation to collect cells. The collected cells were suspended in 2.5 ml of 0.1 M aqueous MgCl₂ solution. The cell suspension was then subjected to low-speed centrifugation to collect cells. The cells were suspended in 1.2 ml of 0.1 M aqueous CaCl₂ solution and the resulting cell suspension was allowed to stand at 0° C. for 30 minutes, followed by low-speed centrifugation to collect cells. The collected cells were resuspended in 0.1 ml of 0.1 M aqueous CaCl₂ solution. To the resulting cell suspension was added 10 μl of the ligated DNA solution as prepared in Step 3. The resulting mixture was allowed to stand on iced water for 30 minutes and then heated in a 40° C. water bath for 5 minutes. 1.0 ml of LB medium pre-warmed at 37° C. was added to the heated mixture, followed by incubation at 37° C. for 90 minutes. Then, 0.1 ml of the obtained culture broth and 0.1 ml of the culture broth diluted 10 times with LB medium each were spread on T agar plates containing tetracycline or ampicillin and then incubated at 37° C. or 30° C. overnight to form colonies of transformants resistant to tetracycline or ampicillin. The formed transformant colonies were sprayed with an alkaline phosphatase detecting dye solution [containing 2 mg/ml of α-naphthylphosphate and 20 mg/ml Fast Blue B Salt (tetrazotized o-dianisidine)] dissolved in 0.5 M Tris-HCl (pH 8.0). The white transformant colonies which had not changed to brown by spraying the dye solution were selected as the cells carrying the plasmids in which the E. coli phoS gene was ligated to pBR322 DNA.

B: E. coli C2 strain

Substantially the same procedures as mentioned just above were repeated to select white transformant colonies containing plasmids in which an E. coli phoS gene was ligated to pBR322 DNA, except that the transformation of E. coli C2 strain [Morris, H., M. J. Schlesinger, M. Bracha, and E. Yagil, J. Bacteriol., 119, 583–592 (1974)] was used as the indicator of the selection of the plasmids.

Steps 5: Construction of restriction maps of plasmids (pSN401 and pSN402) carrying a phoS gene The transformants as selected in the above Steps 4 were cultured in LB medium. Then, plasmid DNAs were extracted from the obtained cultured cells and purified as follows. Plasmid DNAs were extracted from the above-obtained cultured cells according to the rapid alkali extraction method. Then, the crude plasmid DNA solutions were purified by equilbrium density-gradient centrifugation in the same manner as in Step 1. Ethidium bromide was removed from the thus purified plasmid DNA solutions and DNA was precipitated (see Step 1). The thus obtained plasmid DNAs were digested with various restriction enzymes and, then, the lengths of DNA fragments were determined by electrophoresis on agarose gel. The restriction maps of the plasmids were constructed. As a result, it was found that two kinds of plasmids carrying the phoS gene had been prepared. One of the plasmids is hereinafter referred to as "pSN401" and the other "pSN402". The restriction map of the plasmid pSN401 is shown in FIG. 1. In the plasmid pSN402, the $EcoRI_1$–$EcoRI_2$ fragment of pSN402 was inserted in the opposite orientation to that of the plasmid pSN401.

EXAMPLE 2

Step 1: Preparation of bacteriophage λglmS DNA fragments containing the phoS gene 150 ml of T medium was inoculated with 1.5 ml of a seed of *Escherichia coli* KY7388 strain [T. Miki, Annu. Rep. Inst. Virus Res., 21, 1–26 (1978)] which is a lysogen of bacteriophage λglmS, and cultured at 37° C. with shaking. At the middle logarithmic growth phase, mitomycin C was added to the culture to the final concentration of 0.5 μg/ml. The culture was continued for further about 2 hours until lysis. The culture was cooled on ice, and chloroform was added dropwise (several drops) thereto. Thereafter, air was pipetted into the culture broth to cause the culture broth to bubble, whereby the cells in the culture broth were completely lysed. The resulting phage lysate was then subjected to low-speed centrifugation. The supernatant was collected while the precipitant consisting of cell debris were discarded. The obtained supernatant was subjected to high speed centrifugation at 25,000 rpm for 90 minutes to collect λglmS phage particles precipitated at the bottom of the centrifugation tube. The collected phage particles were suspended in 4.0 ml of λ diluent [containing 10 mM Tris-HCl (pH 7.5), 10 mM $MgSO_4$ and 0.1 mM $Na_2EDTA$]. The resulting phage particle suspension was subjected to CsCl block density-gradient contrifugation, followed by CsCl equibibrum density-gradient centrifugation to obtain a fraction containing only λglmS phage particles. λglmS DNA was extracted from the above-obtained λglmS phage particles using formamide in the manner as described below. Specifically, to 0.5 ml of the λglmS phage particles fraction were added 0.05 ml of a Tris-EDTA solution[containing 2 M Tris-HCl (pH 8.5) and 0.2 M $Na_2EDTA$] and then 0.5 ml of formamide. The resulting mixture was allowed to stand at room temperature for about 3 hours. Then, 0.5 ml of distilled water and 3 ml of absolute ethanol were successively added to the mixture and mixed to precipitate λglmS phage DNA. The precipitated λglmS phage DNA was collected by centrifugation, washed with 70 v/v % ethanol and vacuum-dried to obtain a dried λglmS DNA. The dried λglmS DNA was dissolved in 5 ml of a Tris-EDTA solution [containing 10 mM Tris-HCl (pH 7.5) and 1 mM $Na_2EDTA$] and then cleaved by a restriction enzyme EcoRI and dialyzed in the same manner as in Step 2 of Example 1. Thus, a solution containing DNA fragments carrying the phoS gene was prepared.

Step 2: Ligation of pBR322DNA and λglmS phage DNA fragments containing phoS gene Substantially the same procedures as in Step 3 of Example 1 were repeated to prepare a ligated DNA solution, except that the λglmS phage DNA solution as prepared in Step 1 above was used instead of the E. coli DNA solution.

Step 3: Selection of plasmids carrying the phoS gene

A: E. coli C75 strain

Substantially the same procedures as in step 4-A of Example 1 were repeated to select white transformant colonies carrying the plasmids containing the phoS gene prepared from λglmS phage, except that the ligated DNA solution as prepared in the above step 2 was used instead of the ligated solution as prepared in Step 3 of Example 1.

B: E. coli C2 strain

Substantially the same procedures as in Step 4-B of Example 1 were repeated to select white transformant colonies containing plasmids in which the phoS gene prepared from λglmS phage was ligated to pBR322 DNA, except that the ligated DNA solution as prepared in the above Step 2 was used instead of the ligated solution as prepared in Step 3 of Example 1.

Step 4: Construction of restriction maps of plasmids (pSN401 and pSN402) carrying the phoS gene Substantially the same procedures as in step 5 of Example 1 were repeated to construct restriction maps of plasmids, except that the plasmids as obtained in the above Step 3-A and Step 3-B were used instead of the plasmids as obtained in step 4A and Step 4-B of Example 1. As a result, it was found that the plasmids obtained in the above steps were pSN401 and pSN402.

EXAMPLE 3

Step 1: Construction of plasmid pSN507 carrying the phoS gene from pSN401

The pSN401 DNA as obtained in Step 5 of Example 1 was partially digested with restriction enzyme HindIII and, then, religated by using T4 ligase in substantially the same manner as described in Step 3 of Example 1. Using the thus obtained religated plasmid solution, E. coli C75 strain and C90 strain [Garen, A., and N. Otsuji, J. Mol. Biol., 8, 841–852 (1964)] as recipients were transformed in substantially the same manner as described in Step 4 of Example 1 to obtain strains carrying the phoS+ plasmids. Then, plasmid DNAs were extracted from the cultures of the several independent transformants and purified in substantially the same manner as described in Step 5 of Example 1 and a restriction map of the plasmids were constructed. The purified religated plasmid is hereinafter referred to as "pSN507" whose physical map is shown in FIG. 1.

Step 2: Construction of plasmid pSN508 carrying the phoS gene from pSN507

The pSN507 DNA obtained in the above Step 1 was digested with restriction enzyme MluI and, then, the religation of the plad and the transformation of each of E. coli C75 strain and E. coli C 90 strain with the religated plasmid were carried out in substanttally the same manner as described in the Step 3 of Example 2 to obtain strains carrying the resulting reconstructed plasmid (hereinafter referred to as "pSN508"). Then pSN508 DNA was extracted from the cultured cells of the thus obtained strains and purified in substantially the same manner as described in Step 5 of Example 1. A restriction map of the plasmid pSN508 was constructed. The result is shown in FIG. 1.

Step 3: Construction of plasmid pSN518 carrying the phoS gene from pSN508

The pSN508 DNA obtained in the above Step 2 was digested with restriction enzyme pstI and, then, the religation of the plasmid and the transformation of each of E. coli C75 strain and E. coli C90 strain with the religated plasma were carried out in substantially the same manner as described in the above Step 2 to obtain strains having the reconstructed plasmid (hereinafter referred to as "pSN518"). Then, pSN 518 DNA was extracted from the cultured cells of the thus obtained strains and purified in substantially the same manner as described in Step 5 of Example 1. A restriction map of the plasmid pSN518 was constructed. The result is shown in FIG. 1.

EXAMPLE 4

Construction of plasmids pSN407 and pSN408 carrying the phoS gene from pSN402

The pSN402 DNA obtained in step 5 of Example 1 was reconstructed in substantially the same manner as described in step 1 of Example 3. The resulting plasmid is hereinafter referred to as "pSN407". Then, a restriction map of the plasmid pSN407 was constructed. The restriction map of pSN407 was substantially the same as that of pSN507, except that the orientation of the EcoRI$_1$-EcoRI$_2$ fragment of pSN407 was opposite to the orientation of that of pSN507.

The above-obtained pSN407 was reconstructed in the same manner as in step 2 of Example 3. The resulting plasmid is hereinafter referred to as "pSN408". The restriction map of pSN408 was constructed. The restriction map of pSN408 was substantially the same as that of pSN508, except that the orientation of the EcoRI$_1$-EcoRI$_2$ fragment of pSN408 was opposite to the orientation of that of pSN508.

EXAMPLE 5

Construction of plasmids pSN1507 and pSN1508 carrying the phoS gene from pSN507

In substantially the same manner as described in Example 1, plasmid pBR325 [Bolivar, F. et al., Gene, 4, 121 (1978)] and plasmid pSN507 each were cleaved with restriction enzyme EcoRI. Then, the cleaved pBR325 was ligated to the cleaved pSN507 in substantially the same manner as described in step 3 of Example 1. Then, in substantially the same manner as described in step 4 of Example 1, screening of the obtained ligated DNA was carried out using E.coli ANCC75 strain [a P1 transduction product: E. coli C75 strain X E. coli CSH57 strain (Miller, J. H., Experiments in molecular genetics, Cold Spring Harbor Laboratory, Cold Spring Harbor, N.Y., pp 13-23 (1972)] as a recipient.

Substantially the same procedures as in Step 5 of Example 1 were repeated to extract and purify the above-obtained plasmids. The restriction maps of the plasmids were constructed. As a result, it was found that two kinds of plasmids containing the phoS gene had been obtained. One of the plasmids is hereinafter referred to as "pSN1507" and the other "pSN1508". It was also found that the EcoRI$_1$-EcoRI$_2$ fragment of pSN507 had been inserted into the EcoRI site of pBR325 to form pSN1507.

EXAMPLE 6

Construction of plasmid pSN2507 carrying the phoS gene and construction of a restriction map of the plasmid pSN2507

Plasmid pKN402A [B. E. Uhlin et al., Gene, 6, 91-106 (1979)] DNA of which the restriction map is shown in FIG. 2 was partially digested with restriction enzyme HincII and religated with T4 ligase. Strains having religated plasmids (hereinafter referred to as "pSH101") were obtained in substantially the same manner as described in step 4 of Example 1 and step 5 of Example 1 and a restriction map of the pSH 101 was constructed. The restriction map is shown in FIG. 2. pSH101 and pSN507 each were digested with EcoRI. The obtained fragments of pSH101 and pSN507 were ligated by using T4 ligase. The obtained ligated plasmid was subjected to screening to obtain white transformant colonies having plasmids carrying the phoS gene and formed by ligation of the fragment of pSN507 to pSH101. The obtained transformant colonies were cultured and plasmid DNAs were extracted from the cultured transformants and purified in substantially the same manner as described in Step 5 of Example 1. A restriction map of the plasmid pSN2507, one of the plasmids thus obtained, was constructed in substantially the same manner as described in Step 5 of Example 1. The location of the phoS gene in pSN2507 was determined. The restriction map of pSN2507 is shown in FIG. 2. It was found that a plasmid in which the orientation of the EcoRI$_1$-EcoRI$_2$ fragment carrying the phoS gene was inserted in the opposite orientation to that of pSN2507 had been prepared also in the above ligation of the pSN507 fragment to pSH101.

EXPERIMENT 1

The power of gene expression of the expression vector of the present invention was determined by calculating the number of molecules of the phosphate-binding protein produced per host cell. The mechanism of the production of a phosphate-binding protein by means of the expression of the phoS gene will be briefly explained below. The precursor of the phosphate-binding protein is first produced by the expression of the phoS gene. The precursor has a signal peptide at the N-terminal of the mature phophate-binding protein. The signal peptide is required for interaction with and secretion through the inner membrane. Therefore, the precursor of the phosphate-binding protein is first transported to the inner membrane by the function of the signal peptide. Then, the signal peptide portion of the protein is cleaved while it passes through the inner membrane and the cleaved mature phosphate-binding protein is secreted into the periplasm of the cell.

The determination of the number of molecules of the phosphate-binding protein produced per cell was effected as follows.

E. coli ANCC 75 strain was transformed with the plasmid pSN507 and incubated overnight in Tris/-glucose medium which is a minimal salt solution buffered with Tris/HCl (pH 7.2) containing 0.2% (w/v) of glucose and supplemented with 0.64 mM of KH$_2$PO$_4$ (hereinafter referred to as "high-phosphate medium"). After incubation, the host cells were harvested and suspended in two kinds of culture media, namely, the above-mentioned high-phosphate medium and the same Tris/glucose medium as described above except that the concentration of KH$_2$PO$_4$ was 0.064 mM (hereinafter referred to as "low-phosphate medium"), followed by incubation at 37° C. with shaking for 6 hours. The cell density of each culture was estimated from the absorbance at 600 nm. As a result, it was found that the number of cells in each culture was $1.3 \times 10^9$. Then, the cells in each culture were collected by centrifugation at 2000 X g for 5 min.

The collected cells were washed once with 1 ml of buffer solution containing 10 mM Tris-HCl(pH 7.2) and 30 mM of NaCl, and resuspended in 0.1 ml of 33 mM Tris-HCl (pH 7.5) in a centrifugation tube. 0.1 ml of buffer solution containing 33 mM of Tris-HCl (pH 7.5), 40% (w/v) sucrose and 0.1 mM EDTA was added to the above-mentioned cell suspension, mixed rapidly and incubated at 37° C. for 10 min. The cells were collected by centrifugation at 8000 X g for 3 min and immediately resuspended in 0.1 ml of 0.5 mM aqueous MgCl solution. The cell suspension was vigorously shaken in an iced water bath for 10 min, followed by centrifugation at 8000 X g for 5 min. To the thus obtained supernatant (hereinafter referred to as "periplasmic fraction") was added 20 μl of a sample buffer solution for polyacrylamide electrophoresis [containing 1 ml of 0.5 M Tris-HCl (pH 6.8), 1 ml of 10 w/v% sodium dodecyl sulfate (SDS), 0.1 ml of β-mercaptoethanol, 1 ml of glycerol, 2.5 ml of 0.1 w/w % aqueous solution of bromphenol blue and 4.4 ml of water], followed by heat treatment at 100° C. for 5 min. The pellet (hereinafter referred to as "intracellular fraction") obtained in the above-mentioned centrifugation was washed twice with 1 ml of 0.5 mM aqueous MgCl$_2$ solution and resuspended in 20 μl of the lysozyme solution [containing 2 mg of lysozyme in 1 ml of water, 50 mM glucose, 10 mM EDTA and 25 mM Tris-HCl (pH 8.0)], followed by incubation at 37° C. for 30 min. The thus obtained suspension was diluted with 180 μl of 0.5 M aqueous MgCl$_2$ solution and the mixture was sufficiently stirred. Then, to the mixture was added 120 μl of the above-mentioned sample buffer solution for polyacrylamide electrophoresis, followed by heat treatment at 100° C. for 5 min.

The above-prepared fractions were subjected to SDS-polyacrylamide gel electrophoresis according to the procedure as described in Laemmli, U.K., Nature, 227, 680–685 (1970), whereby the yield of the phosphate-binding protein in the cells was determined. The results are shown in Table below.

TABLE

| | Amount (μg/cell) | |
|---|---|---|
| | low-phosphate medium | high-phosphate medium |
| Phosphate-binding protein | $8.0 \times 10^{-8}$ | $1.0 \times 10^{-11}$ |

As is apparent from the above Table, the production of the phosphate-binding protein and the precursor thereof, in other words, the expression of the gene coding for a phosphate-binding protein of the expression vector of the present invention is controlled by adjusting the concentration of phosphate in the culture medium.

Then, the number of molecules of the phosphate-binding protein per cell was calculated by the following equation:

$$\text{The number of molecules per cell} = \frac{A}{B} \times C$$

wherein A is the yield of the phosphate-binding protein (g/cell); B is the molecular weight of the phosphate-binding protein (35,000); and C is Avogadro's number ($6 \times 10^{23}$).

The number of molecules of the phosphate-binding protein was $1.3 \times 10^6$ per cell when cultured in low-phosphate medium.

EXAMPLE 7

Production of β-galactosidase by using the plasmid pSN508 carrying the phoS gene The plasmid pSN508 as prepared in Step 2 of Example 3 was cleaved by using EcoRI, thereby to prepare an EcoRI-EcoRI DNA fragment carrying a phoS gene. To the thus prepared DNA fragment carrying the phoS gene was ligated the DNA fragment prepared by cleaving the plasmid pMC1403 containing a gene coding for β-galactosidase [with respect to plasmid pSN1403, reference may be made to Journal of Bacteriology, 143, 971–980 (1980)] by means of EcoRI, thereby to form a recombinant vector.

Then, the recombinant vector (hereinafter referred to as "pSN5081") was selected and isolated in substantially the same manner as described in Step 4 and Step 5 of Example 1.

Subsequently, the plasmid pSN5081 was partially deleted by using HpaI. Then, the both terminals of the resulting DNA fragment of plasmid pSN5081 was partially digested by using the Nuclease BAL31 (trade name of deoxyribonuclease manufactured and sold by Bethesda Research Laboratories Inc., U.S.A.) and subjected to cleaving by using SmaI. The cleaved DNA fragment of the plasmid was religated by using T4 ligase.

Then, E. coli CSH26 strain [reference may be made to J. H. Miller, Experiments in Molecular Genetics, Cold Spring Harbor Laboratory, p 17 (1972)] which is a Lac$^-$ mutant incapable of utilizing lactose in a culture medium was transformed in a lactose-added tetrazolium plate as the culture medium with the above-obtained recombinant vector carrying a gene coding for β-galactosidase to form transformants. The phenotype Lac$^-$ of E. coli CSH26 strain became Lac$^+$ by transformation with the recombinant vector and, therefore, the above-obtained transformants were changed so that they were capable of utilizing lactose in the lactose-added tetrazolium plate. Accordingly, the transformants were easily selected from parent cells of *E. coli* CSH26 strain using as a criterion the size and colour of the colonies formed on the lactose-added tetrazolium plate in substantially the same manner as described in Experiments in Molecular Genetics, Cold Spring Harbor Laboratory, p 49 and pp 52-54 (1972). The religated plasmid is hereinfter referred to as "pSN5084". In the plasmid pSN5084, the DNA fragment carrying the gene coding for β-galactosidase was ligated to the DNA fragment carrying the phoS gene at its portion downstream of the DNA sequence of a promoter of the phoS gene, so that to β-galactosidase could be produced in the form of a fusion protein.

Then, *E. coli* CSH26 strain was transformed with the plasmid pSN5084 to form transformants. The selection of the transformants from parent cells of *E. coli* CSH26 strain was carried out in the same manner as described above. The selected transformants were incubated in low-phosphate medium, thereby to produce β-galactosidase in the form of the fusion protein. Then, the specific activity of β-galactosidase in the transformants was determined according to the procedure as described in Experiments in Molecular Genetics, Cold Spring Harbor Laboratory, pp 352-355 (1972). The number of molecules of the βgalacptosidase produced in the form of the fusion protein per cell was calculated by comparing the specific activity of the β-galactosidase produced in the form of the fusion protein with the specific activity of a standard β-galactosidase having a molecular weight of 145,000. As a result, it was found that the number of moleculues of the β-galactosidase produced in the form of the fusion protein per cell was $1 \times 10^5$.

What is claimed is:

1. An expression vector which consists essentially of a DNA fragment of a phoS gene of Enterobacteriaceae and a replicon selected from the group consisting of plasmids and bacteriophages, said DNA fragment being ligated to said replicon.

2. A method for preparing an expression vector which comprises:
   (1) isolating a chromosomal DNA containing a phoS gene from bacterial belonging to Enterobacteriaceae;
   (2) cleaving the chromosomal DNA with a restriction enzyme to provide DNA fragments;
   (3) ligating said DNA fragments to a replicon selected from the group consisting of plasmids and bacteriophages;
   (4) transforming cells of a bacterium belonging to Enterobacteriaceae with said replicon having the DNA fragment ligated thereto form transformants comprising those which contain a recombinant vector consisting essentially of the DNA fragment of a phoS gene and a replicon;
   (5) selecting transformants containing the recombinant vector consisting essentially of the DNA fragment of a phoS gene and the replicon from said transformants;
   (6) isolating the recombinant vector consisting essentially of the DNA fragment of the phoS gene and the replicon from the selected transformants.

3. A method according to claim 2, which further comprises cleaving two sites of the isolated recombinant vector consisting essentially of the DNA fragment of a phoS gene by means of a restriction enzyme so that part of the recombinant vector defined by said two sites is deleted while retaining the phoS gene and a replicon, and subjecting the resulting partially deleted recombinant vector to religation by means of ligase to prepare a reconstructed expression vector.

4. A method according to claim 2, which further comprises cutting out the DNA fragment of a phoS gene from the isolated recombinant vector, and ligating the cut-out DNA fragment to a replicon selected from the group consisting of plasmids and bacteriophages which is of a different kind from the kind of replicon of said isolated recombinant vector.

5. A method for producing a polypeptide by means of gene expression using an expression vector consisting essentially of a DNA fragment of a phoS gene of Enterobacteriaceae and a replicon selected from the group consisting of plasmids and bacteriophages, said DNA fragment being ligated to said replicon which comprises:
   (1) ligating a DNA fragment carrying a gene coding for a polypeptide to said expression vector at a position downstream of the DNA sequence of a promoter of the phoS gene;
   (2) trasforming cells of a bacterium belonging to Enterobacteriaceae with said expression vector having the gene coding for a polypeptide ligated thereto to form transformants;
   (3) selecting said tranformants from parent cells of a bacterium belonging to Enterobacteriaceae;
   (4) incubating said transformants, causing said transformants to express the gene coding for the polypeptide and produce the polypeptide; and
   (5) isolating the polypeptide from the incubated transformants.

6. A method according to claim 5, wherein in the step (1), said position is between the proximal part and the distal part of the DNA fragment of a phoS gene.

7. A method according to claim 5, wherein in the step (1), said position is downstream of the DNA fragment of a phoS gene.

* * * * *